United States Patent [19]

Dabi

[11] Patent Number: 4,613,543
[45] Date of Patent: Sep. 23, 1986

[54] INTERPENETRATING POLYMERIC NETWORK FOAMS COMPRISING CROSSLINKED POLYELECTROLYTES

[75] Inventor: Shmuel Dabi, Highland Park, N.J.

[73] Assignee: Personal Products Company, Milltown, N.J.

[21] Appl. No.: 604,710

[22] Filed: Apr. 27, 1984

[51] Int. Cl.[4] ............................................... B32B 3/26
[52] U.S. Cl. ................................. 428/304.4; 525/375; 521/134; 521/137; 521/139; 521/86
[58] Field of Search ..................... 428/304.4; 525/375; 521/137, 134, 139, 86

[56] References Cited

U.S. PATENT DOCUMENTS

| | | | |
|---|---|---|---|
| 3,393,168 | 7/1968 | Johnson | 524/539 |
| 3,514,419 | 5/1970 | Darlow et al. | 525/117 |
| 3,557,067 | 1/1971 | Burns et al. | 524/549 |
| 3,806,498 | 4/1974 | Wilson et al. | 525/375 |
| 3,907,756 | 9/1975 | Marx et al. | 525/375 |
| 4,076,673 | 2/1978 | Burkholder, Jr. | 524/389 |
| 4,310,593 | 1/1982 | Gross | 524/556 |

FOREIGN PATENT DOCUMENTS

| | | | |
|---|---|---|---|
| 42-22044 | 10/1967 | Japan | 525/375 |
| 56-131616 | 10/1981 | Japan | 521/137 |
| 744027 | 1/1956 | United Kingdom | 521/137 |
| 898272 | 6/1962 | United Kingdom | 521/137 |
| 1137465 | 12/1968 | United Kingdom | 521/137 |

*Primary Examiner*—Joseph L. Schofer
*Assistant Examiner*—N. Sarofim
*Attorney, Agent, or Firm*—Jason Lipow

[57] ABSTRACT

An absorbent body for absorbing body fluids is provided which is highly liquid retentive and comprises cellular polymeric absorbent material. The absorbent body of the invention comprises a cellular interpenetrating polymeric network comprising a crosslinked polyelectrolyte.

16 Claims, No Drawings

INTERPENETRATING POLYMERIC NETWORK FOAMS COMPRISING CROSSLINKED POLYELECTROLYTES

BACKGROUND OF THE INVENTION

This invention concerns providing cellular polymers suitable for use in products for absorbing body fluids such as for example, sanitary napkins, catamenial tampons, diapers, bandages, surgical dressings and the like. Such materials, commonly referred to as foams have already been considered for use in such products and in this connection, polyurethane foams, polyester foams and cellulose foams have been suggested.

While these foams, in the main, have been capable of absorbing body fluids to varying degrees, their properties have fallen short of those preferred for products such as diapers, sanitary napkins and the like. One such shortcoming is that while these foams may be formulated to be hydrophilic and hence initially take up large quantities of aqueous liquids, when subjected to pressure such liquid is easily expressed, i.e., the fluid retention properties of these foams are poor. The reason for this is that most of the liquid held by the foam is mechanically held in the cellular void spaces and every deformation caused by external pressure tends to collapse the cell walls, reduce the available void volume and hence express the liquid. Needless to say, such deforming pressure is to be expected in absorbent products worn by the user.

It has been suggested that the fluid retention may be improved by incorporating additional absorbent polymers into the foam. Such additional polymers, commonly called hydrocolloids or superabsorbents are water insoluble, swellable, polyelectrolytes capable of holding many times their weight of liquids and retaining these liquids under pressure. The insoluble polyelectrolytes are blended into the foaming mixture as solid particles during the foaming reaction which forms the foam and hence are distributed in the finished foam matrix. Such a technique is described in U.K. Pat. No. 1,550,614. Unfortunately, it has been found that when the resulting material is wet with body fluids, some of the swollen gel-like superabsorbent is easily, detached from the foam matrix thus reducing its efficiency in retaining liquids within the cells of the foam. Additionally, it has been found that a substantial portion of the superabsorbent is encapsulated in the polymeric foam matrix and hence is inhibited from contact with the liquid and restricted in its abilities to swell and retain liquid.

Accordingly, there is a need for a better way of providing liquid retentive cellular polymeric absorbent materials.

SUMMARY OF THE INVENTION

In accordance with the teachings of this invention, a cellular polymeric material, i.e., a foam, is provided for absorbent products which cellular polymeric material exhibits greatly improved water retentive properties without the drawbacks encountered by prior attempts to render such cellular polymeric material retentive. Specifically, this invention is directed to providing, as an absorbent body for absorbing body fluids, a cellular interpenetrating polymeric network comprising a crosslinked polyelectrolyte.

Interpenetrating polymer networks (IPN's) are already known in the prior art as exemplified by Sperling, L. H., J. Poly. Sci. Macronol Rev., 12, 141, (1977); Frisch, H. L., Frisch, K. C., Klempner, D., Chemtech, 7, 188, (1977); Lipatov, Yu, S., Sergeva, L. M., Russ, Chem., Rev, 45, 63, (1976); and Jerome, R., Desreux, V., J. Appl. Poly. Sci., 15, 199 (1971). They may be defined as polymer mixtures consisting of two or more polymer networks synthesized within each other. On the molecular level, they can be viewed as interlocked molecules of two species which are not chemically bonded to each other but physically inseparable. Said in other words, polymer mixtures are often thermodynamically unstable and therefore tend to phase separate. On the other hand, in the case of IPN's, the interlocking at the molecular level tends to avoid such separation.

Different synthesis routes for obtaining IPN's have been described, the three main ones being:

(1) synthesis of one polymer network, followed by imbibing it with the monomer of a second polymer, followed by polymerization and crosslinking, the product being referred to as a sequential IPN;

(2) mixing two prepolymers of different kinds, followed by polymerization and crosslinking through an independent mechanism so as to avoid chemical bonding between the two systems, the product being referred to as a simultaneous IPN; and (3) synthesis of one polymer network, followed by imbibing it with a monomer of a second polymer without a crosslinking agent so that upon polymerization a linear polymer is obtained which is not interlocked yet is intimately entangled with the first network, the product being referred to as a pseudo IPN.

This invention contemplates the formation of all three types of IPN's wherein at least one of the polymer networks in the system is a formed i.e., cellular, polymer and the other is a crosslinked polyelectrolyte. The foamed polymer may be formed from precursors such as polymers, reactive oligomers, monomers or other components capable of being roamed into a cellular polymer.

Polymers which may be employed are available in the form of water based latices such as, for example water latices of styrene-butadiene, styrene-butadiene acrylonitrile, polyurethane, epoxy, or acrylic latices.

Reactive oligomers usable are, for example, isocyanate terminated polyurethanes, polyesters having unsaturated carbon-to-carbon bonds, epoxy oligomers, aminoplasts (e.g., melamine formaldehyde, urea formaldehyde), or phenolic resins.

A usable monomer may be, for example, an isocyanate of epoxy compound.

The polyelectrolates and crosslinking agents combined with the foamable prepolymers are provided and crosslinked during the foaming process or after but are not crosslinked prior to the foaming process. They are chosen such that they will crosslink through their carboxylic acid functions only and will not react with the foamable polymer. As a result, a cellular material results which is a physical blend of interlocked polymers and hence an IPN.

In a preferred embodiment, a soft, flexible foam is prepared from a foaming formulation which contains sufficient water to hold in solution a sufficient quantity of a water soluble polyelectrolyte and a crosslinker for such polyelectrolyte. Such a system is, for example, the isocyanate terminated polyether polyols that are currently suggested for use in a one-to-one weight ratio with water to produce hydrophilic polyurethane foams.

Such a foamable polymer system is now sold by the W. R. Grace Company under the tradename Hypol.

DETAILED DESCRIPTION OF THE INVENTION

In the broadest aspects of this invention a cellular interpenetrating polymeric network comprising a crosslinked polyelectrolyte is provided for use as an absorbent for absorbing body fluids. One component of such network comprises a cellular polymer capable of being formed from such precursors as polymers, reactive monomers, or oligomers which can be foamed in the presence of gas. The second component of such a system is a polyelectrolyte, preferably water soluble, which is capable of being crosslinked during or after the foaming process to form the interpenetrating polymeric network with the first component.

The foamed polymer component may be one of many known water dispersions of polymers or oligomers capable of forming a solid foamed material in the presence of gas bubbles such as are introduced by foaming agents or by beating. Examples of such latices are water dispersions of polyurethane, styrene-butadiene copolymers, styrenebutadiene acrylonitrile copolymers, epoxy, acrylic latices including, for example, polymers of ethyl acrylate, methyl acrylate, methyl methacrylate, buthyacrylate and copolymers of these. Other synthetic or even natural rubber latices may be employed.

Additionally, reactive monomers or oligomers capable of polymerizing and foaming in the presence of gas during the foaming process are suitable. For example, epoxy terminated oligomers such as epoxy terminated polyethers, epoxy terminated polyolefin oxides (e.g., polyethylene oxide, polypropylene oxide and copolymers of these) which polymerize in the presence of catalysts such as a tertiary amine of brown trifluoride or polymerize by chain extention with primary or secondary amines. Unsaturated polyester oligomers which polymerize in the presence of a catalyst via free radical polymerization, in combination with a blowing agent, are also suitable. Additionally, aminoplasts such as melamine formaldehyde or urea formaldehyde and phenolic resins are usable, these oligomers being capable of polymerizing in the presence of an acid catalyst.

The system of choice comprises an isocyanate terminated polyurethane oligomer which will polymerize and release carbon dioxide gas during reaction with water and set up to form a solid polyurethane foam. Such a system is the isocyanate terminated polyetherpolyols sold by the W. R. Grace Corporation under the tradename Hypol.

The carboxylic polyelectrolytes component forming the foamed IPN of this invention are known in the art and are described, for example, in U.S. Pat. No. 4,310,593 which is incorporated herein by reference. The essence of usable polyelectrolytes is that they comprise, at least in the salt form, sufficient carboxylate moieties to render them soluble in water and hence capable of being imbibed into the foamed polymer matrix before they are crosslinked. Usable polymers, capable of being prepared from readily available monomers and, if necessary for solubilization, capable of being converted into their salt form, include for example, acrylic acid-acrylate copolymers; acrylic acid-acrylamide copolymers; acrylic acid-olefin copolymers; polyacrylic acid; acrylic acid-vinyl aromatic copolymers; acrylic acid-styrene sulfonic acid copolymers; acrylic acid-vinyl ether copolymers; acrylic acid vinyl acetate copolymers; acrylic acid-vinyl alcohol copolymers; copolymers of methacrylic acid with all of the above monomers; copolymers of maleic acid, fumaric acid and their esters with all of the above comonomers; copolymers of maleic anhydride with all of the above comonomers.

A wide variety of suitable crosslinking agents are usable in accordance with the teachings of this invention, such crosslinking agents being, of course, capable of crosslinking the carboxylic groups of the polyelectrolyte while not reacting to any significant degree with the foamable precursor matrix to thereby form the IPN of this invention. Such suitable crosslinking agents are described in U.S. Pat. No. 4,008,353 and are exemplified by polyhaloalkankols such as 1,3-dichloroisopropanol, 1,3-dibromoisopropanol; sulfonic zwitterions such as the tetrahydrothiophene adduct of novolac resins; haloepoxyalkenes such as epichlorohydrin, epibromohydrin, 2-methyl epichlorohydrin and epiiodohydrin; polyglycidyl ethers such as glycerine diglycidyl ether, ethylene glycol diglycidyl ether, propylene glycol diglycidyl ether, diethylene glycol diglycidyl ether; and mixtures of the foregoing.

A preferred crosslinking agent is that described in my U.S. patent application Ser. No. 604,709 filed on this day for Crosslinked Carboxyl Polyelectrolytes and Method of Making Same. Generally described, such crosslinking agents are low molecular weight, water soluble compounds having at least two functional groups bonded thereto which groups have the general formula:

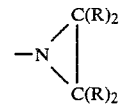

wherein the R groups may be independently selected from the group comprising H, alkyl having from one to three carbon atoms or alkenyl having from one to three carbon atoms. The functional groups are preferably bonded to an aliphatic chain or a substituted aliphatic chain with the essential criterion that such chains be small enough to insure that the compound is water soluble. Preferably the compound has a molecular weight of less than 1000. Such aliphatic or substituted aliphatic chains may include olefinic groups of from 2 to 12 carbon atoms; substituted olefinic groups such as olefinic hydroxides, e.g., butylenehydroxide butylenedihydroxide; mercaptans of olefins such as mercapobutylene ethers of aliphatic compounds such as diethylene glycol or triethylene glycol; esters of aliphatic compounds such as triglycerides or esters of trimethylpropane pentarithisol.

Several such compounds are already commercially available and it will be understood by one skilled in the art that a great many variations of these commercially available compounds can be synthesized while still conforming to the general description given above. A particularly effective group of compounds are the triaziridines based on trimethylolpropane tripropionate adducts having the formula:

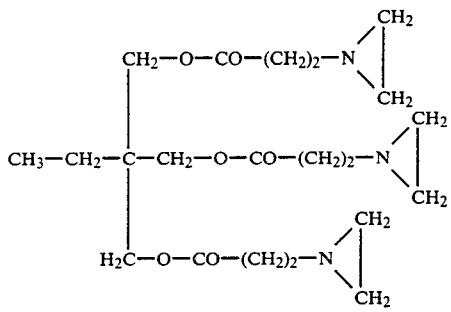

and sold by the Aceto Chemical Company under the trade name TAZ.

Another effective compound, based on pentaerythriol tripropionate adduct, has the formula:

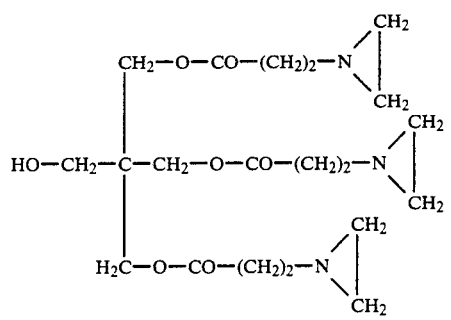

and is sold by Aceto Chemical Company under the trade name TAZO. Similar materials conforming to the general description given above are available from Cordoba Chemical Company under the trade name XAMA. Additionally, other polyfunctional aziridines that have triazine or phosphate backbones are also available. Such are, for example, tris(1-aziridinyl)phosphine oxide, tris(1-aziridinyl)phosphine sulfide; 2,4,6,trisaziridinyl-s-triazine.

The reaction of the functional group of the aziridine with the carboxyl group of a carboxylic polyelectrolyte proceeds rapidly at temperatures of from room temperature or less to about 150° C. with, of course, increasing reaction rate the highest temperatures. The reaction proceeds through ring opening as follows:

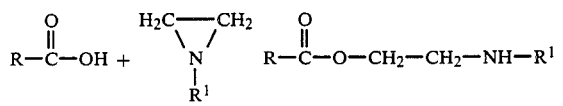

Crosslinking takes place when a polyfunctional aziridine molecule reacts as above with carboxyl groups of adjacent polyelectrolytes to form bridges between these molecules.

The cellular IPN's of this invention are generally synthesized by first forming a water solution of the polyelectrolyte, the crosslinking agent and, optionally, a surfactant. Such surfactant may be included for example, to control the size of the foam cells or to provide the finished product with enhanced wettability. In general terms, the ratio of crosslinker to polyelectrolyte should be, as a minimum, high enough to insure that the polyelectrolyte is rendered insoluble but not so great as to inhibit the swellability of the crosslinked product. Usually no more than 30 parts by weight of crosslinking agent per 100 parts by weight of polyelectrolyte should be employed and preferably less than 20 parts by weight.

When the crosslinking agent is the preferred polyfunctional aziridine, the aziridine is dissolved into the solution at a concentration which may vary from about 0.2 to about 20% by weight, based on the weight of the carboxylic polyelectrolyte. Preferably, the concentration should range from 0.5 to 15% and still more preferably from 1 to 10%. For a given polyelectrolyte, too low a concentration of aziridine will result in a failure to render the polyelectrolyte insoluble. On the other hand, too high a concentration of aziridine will result in a crosslinked product which exhibits relatively low swelling and hence low absorption capacity. These properties also vary with the molecular weight of the uncrosslinked polymer wherein a greater concentration of crosslinking agent is required to insolubilize a low molecular weight polyelectrolyte and a lesser quantity of crosslinker may be employed with higher molecular weight polyelectrolytes. In general, to obtain best absorption properties, the minimum quality of crosslinking agent capable of insolubilizing the polyelectrolyte should be employed.

In accordance with the teachings of this invention, the solution containing the polyelectrolyte, the crosslinking agent and optimally the surfactant, is combined with foamable precursor. The ratio of crosslinked polyelectrolyte to foamable precursor should be high enough so as to effectively enhance the retentivity of the foamed polymer. On the other hand, in the case of the preferred polyurethane oligomer precursors, if too high a ratio is employed the resulting foamed IPN is stiff, nonresilient and tends to produce uncontrollably large cells. Generally, the weight percent of polyelectrolyte based on the weight of foamable precursor should vary between 3 to 50% with 5 to 20% being preferable.

In producing the foaming mixture, sufficient water must be provided in the mixture of foamable precursor, polyelectrolyte, crosslinking agent and surfactant to dissolve the prescribed qualities of polyelectrolyte and crosslinking agent and still carry out the foaming process. In the case of employing latices, i.e., water dispersion sold by various manufacturers, it will be frequently necessary to add additional water to maintain the remaining components in solution.

The following examples illustrate the product of this invention, the method of making the same and the improved properties of the resulting product.

EXAMPLE 1

A solution of 100 grams of water, 12.5 grams of polyacrylic acid (obtained from the Rohm & Haas Company and sold by them under the tradename Acrysol A-5) and 6.5 grams of sodium hydroxide is prepared. The resulting solution of polysodium acrylate is mixed with 0.2 grams of the trifunctional aziridine crosslinking agent obtained from the Aceto Chemical Company and sold by them under the tradename TAZO. The aqueous solution is combined with 100 grams of Hypol 4000 urethane prepolymer obtained from W. R. Grace Company and then is thoroughly mixed by means of a high shear mixer. The mixture is allowed to foam at room temperature and after one hour, is placed in a 65° C. air circulating oven for 12 hours to dry. The resulting foam is soft and has a density of 3.3 lbs/ft³.

A sample of the dry foam, in the form of a two inch diameter, ⅜ inch thick disk, is weighed and then immersed in a beaker of 1% NaCl aqueous solution for one hour. The wet foam is suspended in air for 15 seconds and then reweighed. The foam absorbed 31 grams of the NaCl solution per gram of foam.

The fluid retention of the foam is determined under both static and dynamic pressure conditions. For the static pressure test, the disk sample of the wet foam is rested on a rigid screen. A cast acrylic cylinder confines the sides of the disk and a piston, weighing 2 killograms is inserted into the cylinder to apply pressure on the disk. The piston remains on the sample for 15 minutes whereupon no more fluid is observed as squeezing out of the foam sample through the screen. The sample is then weighed to determine the fluid retained. The sample of this example retained 8 grams of NaCl solution per gram of foam in the static test.

For the dynamic pressure test, higher pressure is applied for a shorter period of time to evaluate the fluid squeeze out under sudden pressure. The wet foam sample is placed between two layers of filter paper and pressure is applied with a 10 lb. roller moving at a constant speed. The procedure is repeated twice, and the foam sample is then reweighed to determine the fluid retained. For the sample of this example, the foam retained 19 grams of NaCl solution per gram of foam.

EXAMPLE 2

Comparative Example

The procedure of Example 1 is followed with the exception that the polyacrylic acid polyelectrolyte is omitted. The resulting foam is soft and has a density of 3.1 lbs/ft³. The absorption capacity of the foam is 29 grams of 1% NaCl aqueous solution, about the same as that of Example 1. The fluid retention of this Example 2 foam, however, is only 4.7 grams of NaCl solution per gram of foam in both the static and dynamic pressure tests.

EXAMPLE 3

The procedure of Example 1 is followed, with the exception that one gram of silicon surfactant obtained from the Union Carbide Corporation and sold by them under the designation L-562, is added to the foaming mixture. The resulting foam has similar properties as those of the Example 1 foam with the exception that larger cells are formed as a result of the inclusion of the surfactant. This structure facilitated the fluid transfer within the foam and increased the absorption rate. It is noted that this wet foam has about a 75% volume increase caused by the swelling of the polyelectrolyte polymer.

What is claimed is:

1. An absorbent body for absorbing body fluids comprising a cellular interpenetrating polymer network wherein a first polymer of said network comprises a foamed polymer and a second polymer of said network comprises a crosslinked polyelectrolyte.

2. The absorbent body of claim 1 wherein said foamed polymer is crosslinked to form a full IPN with said crosslinked polyelectrolyte.

3. The absorbent body of claim 1 wherein said foamed polymer is linear to form a pseudo IPN with said crosslinked polyelectrolyte.

4. The absorbent body of claim 1 wherein said foamed polymer is formed from a foamable polymeric precursor.

5. The absorbent body of claim 4 wherein said foamable polymeric precursor is selected from the group consisting of styrene-butadiene, styrene-butadiene acrylonitrile, urethane, epoxy or acrylic polymers.

6. The absorbent body of claim 1 wherein said foamed polymer is formed from a foamable reactive oligomer precursor.

7. The absorbent body of claim 6 wherein said foamable reactive oligomer precursor is selected from the group consisting of isocyanate terminated polyurethanes, polyesters having unsaturated carbon-to-carbon bonds, epoxy oligomers, aminoplasts or phenolic resins.

8. The absorbent body of claim 1 wherein said foamed polymer is formed from a foamable monomeric precursor.

9. The absorbent body of claim 8 wherein said foamable monomeric precursor is selected from the group consisting of isocyanate or an epoxy compound.

10. The absorbent body of claim 1 wherein said crosslinked polyelectrolyte is formed from a water soluble carboxylic polyelectrolyte.

11. The absorbent body of claim 10 wherein said water soluble carboxylic polyelectrolyte is selected from the group consisting of acrylic acid-acrylate copolymers; acrylic acid-acrylamide copolymers; acrylic acid-olefin copolymers; polyacrylic acid; acrylic acid-vinyl aromatic copolymers; acrylic acid-styrene sulfonic acid copolymers; acrylic acid-vinyl ether copolymers; acrylic acid vinyl acetate copolymers; acrylic acid-vinyl alcohol copolymers; copolymers of methacrylic acid with all of the above monomers; copolymers of maleic acid, fumaric acid and their esters with all of the above comonomers; copolymers of maleic anhydride with all of the above comonomers; and the salt forms of all of the above.

12. An absorbent body for absorbing body fluids comprising a cellular interpenetrating polymer network wherein a first polymer of said network comprises a foam polymer and a second polymer of said network comprises a crosslinked polyelectrolyte and whereas said first polymer is formed from the group consisting of
   (a) foamable polymeric precursors selected from the group consisting of styrene-butadiene, styrene-butadiene acrylonitrile, urethane, epoxy or acrylic polymers;
   (b) foamable reactive oligomer precursors selected from the group consisting of isocyanate terminated polyurethanes, polyesters having unsaturated carbon-to-carbon bonds, epoxy oligomers, aminoplasts or phenolic resins; or
   (c) foamable monomeric precursors selected from the group consisting of isocyanate or an epoxy resin.

13. The absorbent body of claim 12 wherein said foamed polymer is crosslinked to form a full IPN with said crosslinked polyelectrolyte.

14. The absorbent body of claim 12 wherein said foamed polymer is linear to form a pseudo IPN with said crosslinking polyelectrolyte.

15. The absorbent body of claim 12 wherein said crosslinked polyelectrolyte is formed from a water soluble carboxylic polyelectrolyte.

16. The absorbent body of claim 12 wherein said water soluble carboxylic polyelectrolyte is selected from the group consisting of acrylic acid acrylate copolymers; acrylic acid-acrylamide copolymers; acrylic acid-olefin copolymers; polyacrylic acid; acrylic acid-vinyl aromatic copolymers; acrylic acid-styrene sulfonic acid copolymers; acrylic acid-vinyl ether copolymers; acrylic acid vinyl acetate copolymers; acrylic acid-vinyl alcohol copolymers; copolymers of methacrylic acid with all of the above monomers; copolymers of maleic acid, fumaric acid and their esters with all of the above comonomers; copolymers of maleic anhydride with all of the above comonomers; and the salt forms of all of the above.

* * * * *